United States Patent [19]

Perrey et al.

[11] Patent Number: 4,535,111

[45] Date of Patent: Aug. 13, 1985

[54] HEAT SENSITIZING AGENTS, THE PRODUCTION AND USE THEREOF

[75] Inventors: Hermann Perrey, Krefeld; Martin Matner, Odenthal, both of Fed. Rep. of Germany

[73] Assignee: Bayer Aktiengesellschaft, Leverkusen, Fed. Rep. of Germany

[21] Appl. No.: 638,907

[22] Filed: Aug. 8, 1984

[30] Foreign Application Priority Data

Aug. 20, 1983 [DE] Fed. Rep. of Germany ....... 3330197

[51] Int. Cl.³ .................... C08K 5/16; C07C 125/06
[52] U.S. Cl. ........................................ 524/199; 560/26
[58] Field of Search ............................ 524/199; 560/26

[56] References Cited

U.S. PATENT DOCUMENTS

| 3,255,140 | 6/1966 | Sinn et al. | 524/265 |
|---|---|---|---|
| 3,255,141 | 6/1966 | Damm et al. | 524/265 |
| 3,506,605 | 4/1970 | Hornig et al. | 524/747 |
| 3,770,684 | 11/1973 | Singer et al. | 524/199 |
| 3,873,484 | 3/1975 | Bluestein et al. | 524/874 |
| 3,878,152 | 4/1975 | Distler et al. | 524/238 |
| 3,944,690 | 3/1976 | Distler et al. | 427/389 |
| 3,969,289 | 7/1976 | Coffin et al. | 521/70 |
| 4,053,440 | 10/1977 | Bonnet et al. | 524/197 |
| 4,131,603 | 12/1978 | Perrey et al. | 528/49 |
| 4,140,665 | 2/1979 | Perrey et al. | 524/168 |
| 4,190,567 | 2/1980 | Ohmura et al. | 525/452 |
| 4,433,095 | 2/1984 | Hombach et al. | 524/199 |
| 4,472,550 | 9/1984 | Reiff et al. | 524/107 |

FOREIGN PATENT DOCUMENTS

| 1142338 | of 0000 | Canada. | |
|---|---|---|---|
| 756770 | 6/1979 | Fed. Rep. of Germany. | |
| 2822908 | 7/1979 | Fed. Rep. of Germany | 524/199 |
| 7219623 | 10/1968 | Japan. | |
| 53-85894 | 7/1978 | Japan | 524/199 |

Primary Examiner—Joseph L. Schofer
Assistant Examiner—N. Sarofin
Attorney, Agent, or Firm—Connolly and Hutz

[57] ABSTRACT

Certain polyurea-modified polyether urethanes of polyisocyanates, polyethers and polyamines are suitable as heat sensitizing agents for latices.

6 Claims, No Drawings

HEAT SENSITIZING AGENTS, THE PRODUCTION AND USE THEREOF

Heat-sensitized latex mixtures are known. They are usually produced from polymer latices which may be adjusted so that they are sensitive to heat. These latices may be produced by emulsion polymerisation. The heat sensitization thereof and agents which are suitable for this purpose are described in, for example German Pat. Nos. 1,268,828 and 1,494,037.

German Pat. No. 1,243,394 describes a process for the production of synthetic rubber latices which may be rendered sensitive to heat. Heat-sensitized latex mixtures may be used for impregnating fibre webs and for the production of hollow bodies (for example gloves) according to the dip-coating process.

The above-mentioned references describe oxalkylated polysiloxanes in the context of heat sensitizing agents. Moreover, numerous publications disclose other heat sensitizing agents, such as polyvinylalkylethers, polyacetals, cation-active substances, polyetheramines and polyethylene oxides. However, all these compounds suffer from major disadvantages. The disadvantageous properties of polyvinylalkylethers, water-soluble polyacetals, oxalkylated polysiloxanes and cationic materials are stated in German Auslegeschrift No. 2,226,269, column 1, lines 35 to 53. The use of the oxalkylated amines described in the above mentioned Auslegeschrift is, however, also greatly restricted by the necessity of having to adjust to a certain pH value.

German Offenlegungsschrift Nos. 2,516,979 and 2,534,304 describe poyetherurethanes as heat sensitizing agents which are formed by reacting conventional di- and polyisocyanates with preferably monofunctional polyethers. Although these products allow rubber latices to be rendered sensitive to heat where other heat sensitizing agents fail, very large quantities are required for this purpose and thus these products are also unsatisfactory.

Surprisingly, it has now been found that the efficiency of the last-mentioned products is clearly surpassed by polyurea-modified polyetherurethanes which contain two or more urea groups, i.e., it is possible to drastically reduce the quantity required for heat sensitization.

Thus, the present invention provides heat sensitizing agents corresponding to the general formula I

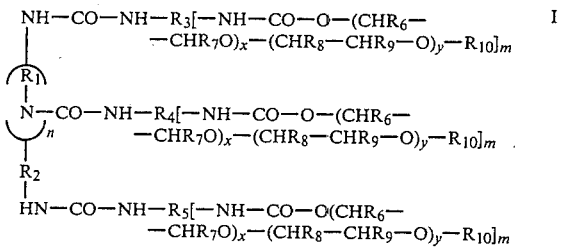

wherein
$R_1$ and $R_2$ independently represent $C_2$-$C_4$ alkylene or $C_3$-$C_{14}$ cycloalkylene,
$R_3$, $R_4$ and $R_5$ independently represent optionally substituted alkylene, cycloalkylene or arylene,
$R_6$, $R_7$, $R_8$ and $R_9$ independently represent hydrogen or methyl,
$R_{10}$ represents $C_1$-$C_{18}$alkyl, $C_6$-$C_{18}$aryl, $C_7$-$C_{18}$aralkyl or $C_2$-$C_{18}$alkenyl,
n represents the values 0 to 50,
m represents the values 1 to 4
x represents the values 5 to 100, and
y represents the values 0 to 100.

Suitable alkylene radicals $R_3$, $R_4$ and $R_5$ are those which have from 1 to 18 carbon atoms, suitable cycloalkylene radicals $R_3$, $R_4$ and $R_5$ are those which have 5 or 6 ring carbon atoms and suitable arylene radicals $R_3$, $R_4$ and $R_5$ are phenylene and naphthylene radicals, and the above-mentioned radicals may contain, for example urethane, uretdion, biuret or isocyanuric acid radicals. The aryl- and cycloalkyl radicals may also be substituted by $C_1$-$C_4$alkyl or chlorine.

Preferred heat sensitizing agents correspond to formula II

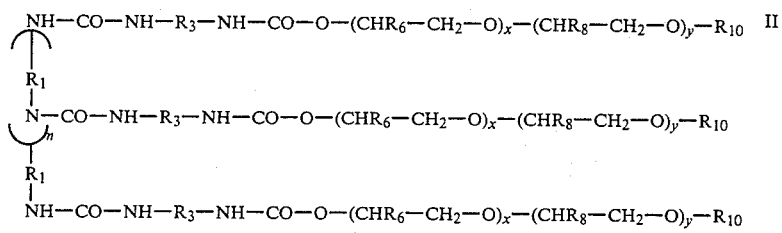

wherein
$R_1$ represents $C_2$-$C_7$alkylene or $C_5$-$C_7$ cycloalkylene,
$R_3$ represents $C_6$-$C_{20}$alkylene or $C_6$-$C_{20}$ cycloalkylene or -arylene which may be substituted by $C_1$-$C_4$alkyl or halogen,
$R_6$ and $R_8$ represent hydrogen or methyl,
$R_{10}$ represents $C_1$-$C_6$alkyl,
n represents the values 0 to 5, and
x and y represent the values 5 to 100,
and the units ($CHR_6$—$CH_2$—O) and ($CHR_8$—$CH_2$—O) are present in blocks, or are statistically distributed or are partially in blocks and partially statistically distributed.

In the case of the most preferred heat sensitizing agents, the symbols in formula II represent the following:
$R_1$ represents $C_2$-$C_3$alkylene,
$R_3$ represents $C_6$-$C_{13}$alkylene, $C_6$-$C_{13}$cycloalkylene or $C_6$-$C_{13}$arylene which may be substituted by methyl,
$R_6$ represents hydrogen,
$R_8$ represents methyl, n represents the values 1 to 5,
x represents the values 5 to 50, and
y represents the values 5 to 40,
and the units (CH$_2$—CH$_2$—O) and (CH(CH$_3$)—CH$_2$—O) are statistically distributed or are partially in blocks and partially statistically distributed.

The polyurea-modified polyether-polyurethanes according to the present invention are obtained by reacting (m+1)-valent polyisocyanates with polyethers corresponding to formula (III)

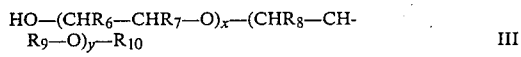
HO—(CHR$_6$—CHR$_7$—O)$_x$—(CHR$_8$—CHR$_9$—O)$_y$—R$_{10}$     III and with polyamines corresponding to formula IV

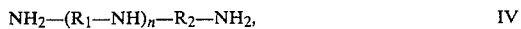
NH$_2$—(R$_1$—NH)$_n$—R$_2$—NH$_2$,     IV wherein the radicals R$_1$, R$_2$, R$_6$, R$_7$, R$_8$, R$_9$, and R$_{10}$ and the values m, n, x and y are as defined above.

The polyisocyanates which are used to produce the polyurea-modified polyether-polyuerethanes may be aliphatic, cycloaliphatic or aromatic. The following are mentioned as examples of suitable polyisocyanates: hexamethylenediisocyanate, cyclohexane-1,4-diisocyanate, 2,4- and 2,6-toluylene diisocyanate, and mixtures thereof, 1-isocyanatomethyl-5-isocyantato-1,3,3-trimethylcyclohexane,(2,2,4- or 2,4,4-trimethyl-hexamethylenediisocyanate-1,6), 1,5-naphthalene-diisocyanate, 1,3-cyclopentylene diisocyanate,m and p-phenylene diisocyanate, 2,4,6-toluylenetriisocyanate, 4,4'4''-triphenylmethanetriisocyanate, 1,3- and 1,4-xylylenediisocyanate, 3,3'-dimethyl-4,4'-diphenylmethanediisocyanate,4,4'-diphenylmethanediisocyanate, 3,3'-dimethylbiphenylenediisocyanate, 4,4'-biphenylenediisocyanate, durenediisocyanate, 1-phenoxy-2,4'-phenylenediisocyanate, 1-tert.-butyl-2,4-phenylenediisocyanate, methylene-bis-4,4'-cyclohexyldiisocyanate, 1-chloro-2,4-phenylenediisocyanate and 4,4'-diphenyletherdiisocyanate.

It is also possible to use relatively high molecular weight and optionally also higher functional polyisocyanates produced from low molecular weight parent substances by a polymerisation reaction to produce uretdions or isocyanurate derivatives. The uretdion of 2 mols of 2,4-toluylenediisocyanate and the polymerisation products, containing isocyanurate rings, of 2,4- and 2,6-toluylenediisocyanate or hexamethylenediisocyanate, a system containing on average 2 isocyanurate rings in the molecule and formed from 5 mols of toluylenediisocyanate, or a corresponding derivative of, on average, 2 mols of toluylenediisocyanate and 3 mols of hexamethylenediisocyanate are mentioned as examples.

According to another synthesis method, it is possible to produce relatively high biuret-linked systems from di- or polyisocyanates by partial hydrolysis via the stage of the carbamic acid and the amine, for example to produce a biuret-linked compound produced formally from 3 mols of hexamethylenediisocyanate with the addition of 1 mol of water and with the release of 1 mol of carbon dioxide.

Equally suitable polyisocyanates are obtained by reacting di- or polyols with di- or polyfunctional isocyanates, if the molar ratio of hydroxy compounds to isocyanate is selected so that in the statistically formed reaction products, free NCO functional groups always remain and so that a molar weight of from 2000 to 3000 is not exceeded.

All the diisocyanates and polyisocyanates described above may be reacted in this manner with diols and polyols, such as mono- and polyethyleneglycol, propanediols, butanediols, neopentylglycol and other pentanediols, adipol, hexanediols, cyclohexanediols, 1,4-dihydroxymethylcyclohexane, perhydrobisphenol A, glycerin, trimethylolethane, trimethylolpropane, other hexane triols and pentaerythritol, under the conditions described above. The reactions of diols and polyols with toluylenediisocyanate are preferred, in which 1 mol of diisocyanate is reacted per OH function.

Diisocyanates are preferably used as polyisocyanates, in particular hexamethylenediisocyanate, isophoronediisocyanate, toluylenediisocyanate and diphenylmethanediisocyanate.

The polyethers used to produce the polyetherurethanes containing urea groups, according to the present invention, are obtained by the polyalkoxylation of alcohols, phenols and alkylphenols having up to 18 carbon atoms. All saturated or unsaturated aliphatic, cycloaliphatic and araliphatic hydroxy compounds which have from 1 to 18 carbon atoms and which may be used for the polyalkoxylation in a pure form or as mixtures are suitable as alcohols.

Ethylene oxide, propylene oxide, 1,2- and 2,3-epoxybutane or epichlorohydrin are included, for example as alkylene oxides for the polyalkoxylation.

Preferred polyethers are obtained by the polyalkoxylation of lower alcohols, such as methanol, ethanol, propanols, butanols, pentanols or hexanols, with ethyleneoxide and propylene oxide. In this process, it is possible to produce block polymers or polymers which have a statistical distribution of the oxyalkyl groups, so-called mixed polymers or to produce mixed forms of these two possibilities. Mixed polymers are preferred, as are those products in which the alcohols are reacted first of all with a mixture of propylene oxide and from 80 to 90% of the total quantity of ethylene oxide to produce mixed polymers, and thereupon the remaining 10 to 20% of ethylene oxide is introduced, so that the end groups of these polyethers are virtually completely primary OH groups. Preferred polyethers contain from 40 to 60% by weight of ethylene oxide and polyethers which are particularly preferred are composed of equal quantities of weight of ethylene oxide and propyleneoxide. Polyethers having molecular weights of from 600 to 5000 are preferably used and those having molecular weights of from 700 to 3000 are more preferably used.

The following are mentioned as aliphatic or cycloaliphatic amines which are suitable for the production of the polyurea-modified polyether polyurethanes according to the present invention: ethylenediamine, diethylenetriamine, triethylenetetramine, tetraethylene pentamine, pentaethylenehexamine, polyethyleneimine, 1,2- and 1,3-propylenediamine, dipropylenetriamine, tripropylenetetramine, butylenediamine, hexamethylenediamine, 2,5-diamino-2,5-dimethylhexane, 2,2,4- and 2,4,4-trimethyl-1,6-hexanediamine, cyclohexanediamine, isophoronediamine, hydrogenated toluylenediamines and hydrogenated diaminodiphenylmethanes.

Preferred polyamines are tri- and higher functional. Diethylenetriamine, triethylenetetramine, tetraethylenepentamine and penta-ethylenehexamine are particularly preferred.

The reaction of the polyisocyanates with the polyethers and the polyamines may be carried out such that a mixture of polyether and polyamine is added dropwise to the polyisocyanate, or, conversely, the polyisocyanate is added dropwise to a mixture of polyether and polyamine. However, these methods often produce insoluble separated materials, and thus the reaction is preferably carried out in two stages. In the first stage, the polyether is reacted with the polyisocyanate, and thereupon the remaining isocyanate groups are reacted with the polyamine. When the polyether is reacted with the polyisocyanate, the polyisocyanate is preferably introduced, and the polyether is added dropwise. For the production of reproducible products, it is important that the polyethers are always used in an anhydrous condition. The reaction may be carried out in inert solvents, such as benzene, toluene, xylene, chlorobenzene, o-dichlorobenzene, acetone and ethylacetate, or without a solvent. It is preferably carried out within a temperature range of from 0° to 140° C. All catalysts which are active in the formation of urethanes (see Houben-Weyl, Methoden der organischen Chemie, Vol. 14.2,p.61, 4th edition, 1963), such as pyridine, methylpyridine, N,N'-dimethylpiperazine, N,N,-dimethylbenzylamine or N,N'-endoethylenepiperazine may be used.

Formulae I and II are idealised structures. Polymer mixtures are formed depending on the reactivity of the reaction components. However, if diisocyanates are used which have isocyanate groups of a different reactivity, such as 2,4-toluylenediisocyanate or isophoronediisocyanate, then it is possible, for the reaction with the polyethers, to first of all react only the more reactive isocyanate group of the molecule in high yields. The formation of the reaction product of 2 mols of polyether and 1 mol of diisocyanate in addition to 1 mol of free diisocyanate, which is possible as a secondary reaction, may be substantially suppressed as a result of careful reaction conditions, so that the compounds according to formulae I and II are substantially obtained after the reaction with the polyamines.

However, if diisocyanates are used which have isocyanate groups of the same reactivity, such as hexamethylenediisocyanate or 4,4'-diphenylmethanediisocyanate, then the reaction with the polyether produces a reaction mixture of 1:1-, 1:2-addition product and unreacted diisocyanate which, after the reaction with the polyamine, thus produces a product mixture of the 1:2-addition product of 1 mol of diisocyanate and 2 mols of polyether, of compounds according to Formula I or II and in particular also of relatively high molecular weight components. These relatively high molecular weight components are synthesized because parts of the molecule, in which not all the NH groups of the polyamine are connected to polyethers via diisocyanates, react with the free diisocyanates by means of the NH groups which are still unreacted, to produce relatively high molecular weight polyureas. Products in which the stoichiometric ratios differ by up to 30% from the ratios given by the formulae are, however, still suitable. In this respect, stoichiometric ratios are preferred in which the total, in terms of mols, of the OH groups and NH groups is the same as that of the isocyanate groups.

In general, the compounds according to the present invention are present as water-soluble or water-emulsifiable oils. Since the efficiency thereof as heat sensitizing agents increases with a good distribution, it is sometimes appropriate, in order to improve the distributing ability to add conventional emulsifiers, for example alkylarylsulphonates, alkylsulphates, fatty acid salts, alkylphenolethoxylates, fatty alcohol ethoxylates or the like.

To produce the heat-sensitizable stable latices themselves, conventional olefinically unsaturated monomers may be polymerised in aqueous emulsion. All radically polymerisable olefinically unsaturated compounds are included as monomers, for example ethylene, butadiene, isoprene, acrylonitrol, styrene, divinylbenzene, alpha-methylstyrene, methacrylonitrile acrylic acid, methacrylic acid, 2-chlorobutadiene-1,3, esters of acrylic acid and methacrylic acid with $C_1$-$C_8$ alcohols or polyols, acrylamide, methacrylamide, N-methylol(meth)acrylamide, (meth)acrylamido-N-methylolmethylether, itaconic acid, maleic acid, fumaric acid, diesters and semiesters of unsaturated dicarboxylic acids, vinylchloride, vinylacetate and vinylidenechloride, which may be used on their own or combined together.

The polymerisation is carried out in the presence of emulsifiers, and the conventional non-ionic or anionic emulsifiers may be used on their own or combined together. The total quantity of emulsifier amounts to from about 0.1 to 10% by weight, based on the monomers.

The emulsion polymerisation may be initiated with radical formers, preferably with organic peroxide compounds which are used in quantities of from 0.01 to 2% by weight, based on the monomers. Depending on the monomer combination, small quantities of regulators may be simultaneously used, for example mercaptans or halogenated hydrocarbons to reduce the molecular weight of the polymer. The emulsion polymerisation may be carried out in two ways. All the monomers and most of the aqueous phase containing the emulsifiers may be introduced, polymerisation may be started by adding the initiator and the rest of the aqueous phase may be added continuously or fractionally during the course of polymerisation. On the other hand, it is possible to employ the "monomer supply" technique. According thereto, only some of the monomers and the aqueous phase containing the emulsifier are introduced and once polymerisation has been initiated, the rest of the monomers and the rest of the aqueous phase is added regularly or intermittently, depending on the conversion. The quantity of monomers which is metered in may be pre-emulsified in the aqueous phase. Both processes are known.

The latices which may be adjusted so that they are sensitive to heat may be mixed with additives before or during processing. Thus, acid cleavers which are also added to the sensitizing agent assist the coagulability in that they reduce the coagulation temperature. Other additives include, for example dyes, pigments, fillers, thickeners, electrolytes, anti-agers, water-soluble resins or vulcanisation chemicals.

Following production, the latices which may be rendered sensitive to heat are adjusted so that they are heat-sensitive by adding the compounds according to the present invention in quantities of from 1 to 20% by weight, preferably from 2 to 15%, based on the polymer. In so doing, the products may be added in 100% or as an aqueous solution, which is often more advantageous. It is found that the heat-sensitive latex mixtures which contain the products of this invention are stable even when they are stored for a comparatively long period of time, and do not show any signs of coagulation.

The latex mixtures of this invention which are adjusted to be sensitive to heat may be used, for example for binding fibre webs which consist of synthetic or natural fibres.

It has proved to be favorable in many cases to reduce the necessary quantity of heat sensitizing agent by adding electrolytes. Suitable electrolytes include, for example NaCl, KCl, NH$_4$Cl, Na-acetate, K-acetate and NH$_4$-acetate, of which from 0.1 to 10% by weight, based on the polymer, is used.

The particular advantage of the heat sensitizing agents according to the present invention is that the electrolyte-containing latex mixtures are extremely stable during storage and when subjected to a mechanical strain, and they do not tend to coagulate prematurely.

EXAMPLE 1

1273 g (1 mol) of a polyether having an OH number of 44, produced by alkoxylating butanol with the same quantities by weight of ethylene oxide and propyleneoxide, (80% of the quantity of ethylene oxide being reacted first of all with all of the propylene oxide in the mixture and then reacting the remaining 20% of ethylene oxide), were added at 50° C. over a period of one hour to a solution of 174 g (1 mol) of 2,4-toluylene diisocyanate and 0.17 g of dibutylditin laurate, and were left to react for about 2 hours.

After 1 mol of isocyanate had thus reacted to produce urethane (a control was carried out by determining the isocyanate number), 34.4 g (0.33 mols) of diethylene triamine were added dropwise at 50° C., and were left to react for 2 hours. A pale yellow, oily, water-soluble liquid was isolated.

EXAMPLE 2 (COMPARATIVE EXAMPLE)

1273 g (1 mol) of a polyether described in Example 1 and having an OH number of 44 were added at 50° C. over a period of one hour to a mixture of 174 g (1 mol) of toluylene diisocyanate, and were then left to react for about 2 hours. After 1 mol of isocyanate had reacted to produce urethane, 1.5 g of finely-ground potassium acetate was added and left to react at 50° C. for about 10 hours. Under these reaction conditions, the second mol of isocyanate reacted, with the formation of isocyanurate, to produce a product which was free of isocyanate groups. Thus, this product contained an isocyanurate link instead of the polyurea modification according to the present invention.

EXAMPLE 3 (COMPARATIVE EXAMPLE)

The process was carried out as described in Example 1, but 44.7 g (0.33 mols) of trimethylol propane were added instead of 0.33 mols of diethylene triamine. The reaction product which was obtained did not contain the polyurea modification of the present invention.

EXAMPLE 4

221 g (1 mol) of 1-isocyanatomethyl-5-isocyanato-1,3,3-trimethylcyclohexane were used analogously to Example 1, instead of toluylene diisocyanate.

EXAMPLE 5

250 g (1 mol) of 4,4'-diisocyanatodiphenylmethane were used analogously to Example 1 instead of toluylene diisocyanate.

EXAMPLE 6

38.7 g (0.167 mols) of pentaethylene hexamine were used analogously to Example 1 instead of 0.33 mols of diethylene triamine. An oil is obtained which is highly viscous at room temperature.

EXAMPLE 7

1870 g (1 mol) of polyether having an OH number of 30 were used analogously to Example 1, instead of the polyether having an OH number of 44. The polyether of OH 30 was also produced by alkoxylating butanol with the same quantities by weight of ethylene oxide and propylene oxide, and 80% of the quantity of ethylene oxide was initially reacted with all of the propylene oxide in the mixture, followed by the remaining 20% of ethylene oxide.

The reaction product dissolved clearly in water.

EXAMPLE 8

168 g (1 mol) of hexamethylene diisocyanate were firstly reacted with 801 g (1 mol) of a polyether having an OH number of 70 which was produced by alkoxylating butanol with the same quantities by weight of ethylene oxide and propylene oxide, and then reacted with 34.4 g (0.33 mols) of diethylene triamine under the reaction conditions described in Example 1.

EXAMPLE 9

168 g (1 mol) of hexamethylene diisocyanate were firstly reacted with 1273 g (1 mol) of the polyether described in Example 1 having an OH number of 44, and then reacted with 34.4 g (0.33 mols) of diethylene triamine under the reaction conditions described in Example 1. The reaction product dissolved clearly in water.

EXAMPLE 10 (COMPARATIVE EXAMPLE)

The process was carried out according to Example 9, except that 44.7 g (0.33 mols) of trimethylol propane were used instead of diethylene triamine. Thus, the reaction product did not contain the polyurea modification according to the present invention, but a urethane link.

EXAMPLE 11 (COMPARATIVE EXAMPLE)

159.3 g (0.33 mols) of a biuret-linked triisocyanate which was produced formally from 3 mols of hexamethylene diisocyanate and 1 mol of water with the release of 1 mol of $CO_2$ was reacted with 1273 g (1 mol) of the polyether described in Example 1 an OH number of 44 under the reaction conditions described in Example 1. The resulting product contained a biuret link instead of the polyurea link according to the present invention.

EXAMPLES 12–18

224 parts by weight of a 40% latex of the copolymer of 64% by weight of butadiene, 31% by weight of acrylonitrile 3.5% by weight of N-methylol acrylamide and 1.5% by weight of acrylamide were mixed with 64 parts by weight of distilled water, 10 parts by weight of 10% sodium hexametaphosphate solution and 60 parts by weight of a heat sensitizing agent, and the coagulation point of the mixtures was determined after a standing time of 30 minutes and 7 days.

METHOD OF DETERMINING THE COAGULATION POINT 10 g of the mixture which had been adjusted to be sensitive to heat were weighed into a beaker and introduced into a water bath having a constant temperature of 80° C. The coagulation behaviour and the rise in temperature were followed by regularly stirring the mixture with a thermometer. The temperature at which a complete and final separation between the polymer and aqueous phase took place was given as the coagulation point of the mixture.

| Example | Heat sensitizing agent according to Example | Coagulation point (°C.) after | |
|---|---|---|---|
| | | 30 Minutes | 7 days |
| 12 | 1 | 43 | 42 |
| 13 | 4 | 49 | 48 |
| 14 | 5 | 44 | 42 |
| 15 | 6 | 41 | 37 |
| 16 | 7 | 47 | 47 |
| 17 | 8 | 35 | 34 |
| 18 | 9 | 41 | 40 |

EXAMPLES 19 AND 20 (COMPARATIVE EXAMPLES)

In these Examples, the charging quantities of the products of Examples 2 and 3 were determined which were required for adjusting the same coagulation point, as it was found for the latex mixture according to Example 12 from 6 g of the heat sensitizing agent of Example 1 according to the present invention.

| Example | Charging quantity (g) | Compound according to Example | Coagulation point (°C.) |
|---|---|---|---|
| 19 | 11 | 2 | 43 |
| 20 | 13 | 3 | 43 |
| 12 | 6 | 1 | 43 |

These Examples clearly show the particular efficiency of the polyurea modification according to the present invention, compared to the isocyanate or urethane link.

EXAMPLES 21 AND 22 (COMPARATIVE EXAMPLES)

In these Examples, the quantities of heat sensitizing agent according to Examples 10 and 11 required for a coagulation point of 41° C. were determined, here again using the latex mixture according to Examples 12 to 18.

| Example | Charging quantity (g) | Compound according to Example | Coagulation point (°C.) |
|---|---|---|---|
| 21 | 14 | 10 | 41 |
| 22 | 12 | 11 | 41 |
| 18 | 6 | 9 | 41 |

These Examples also clearly show the particular efficiency of the polyurea-modified polyurethanes according to the present invention compared to urethane- or biuret-linked types which are otherwise comparable from the point of view of composition.

EXAMPLE 23

The following ingredients were stirred together to produce a latex mixture which is capable of being processed in a heat-sensitive manner:
225.0 parts by weight of a 45% by weight latex of the copolymer of
  66.0% by weight of butadiene,
  30.0% by weight of acrylonitrile, and
  4.0% by weight of methacrylic acid,
40.0 parts by weight of a vulcanisation paste of
  0.2 parts by weight of colloid sulphur,
  0.2 parts by weight of zinc-N,N'-diethyldithiocarbamate,
  1.5 parts by weight of zinc-mercaptobenzthiazole,
  5.0 parts by weight of zinc oxide,
  5.0 parts by weight of titanium dioxide,
  28.1 parts by weight of a 5% aqueous solution of a condensation product of naphthalene sulphonic acid with formaldehyde,
2.0 parts by weight of a 25% by weight aqueous ammonia solution,
54.0 parts by weight of a 40% by weight dispersion of calcium carbonate in water,
84.0 parts by weight of water, and
12.0 parts by weight of the polyether urethane described under Example 1.

The coagulation point of the latex mixture which was measured according to the method described above was 40° C. and was constant for 7 days.

EXAMPLE 24

A latex mixture was produced analogously to Example 23. However, in this case 7.0 parts by weight of the polyether polyurethane of Example 8 were used as the heat sensitizing agent.

The latex mixture had a coagulation point of 43° C. which remained constant for several days.

EXAMPLE 25

62.0 parts by weight of water and 10.0 parts by weight of the polyether polyurethane described in Example 1 are added to 232.0 parts by weight of a 43.5% by weight latex of a copolymer of 46.0% by weight of styrene, 50.0% by weight of butadiene, 2.0% by weight of acrylic acid and 2.0% by weight of N-methylol acrylamide.

The coagulation point of the latex mixture which was produced in this manner and may be rendered sensitive to heat was 38° C. and was constant for several days.

EXAMPLE 26

173.0 parts by weight of a 58% by weight polychloroprene latex,
35.5 parts by weight of a vulcanisation paste of
  7.5 parts by weight of zinc oxide,
  2.0 parts by weight of diphenylthiourea,
  1.0 parts by weight of diphenylguanidine,
  1.0 parts by weight of sulphur, and
  24.0 parts by weight of a 5% by weight aqueous solution of a condensation product of naphthalene sulphonic acid with formaldehyde,
35.0 parts by weight of water,
10.0 parts by weight of a 10% by weight aqueous ammonium chloride solution, and
4.0 parts by weight of the polyether polyurethane described in Example 1 were stirred together.

This latex mixture which was adjusted to be sensitive to heat had a coagulation temperature of 42° C.

We claim:
1. Heat sensitizing agents corresponding to the general formula I

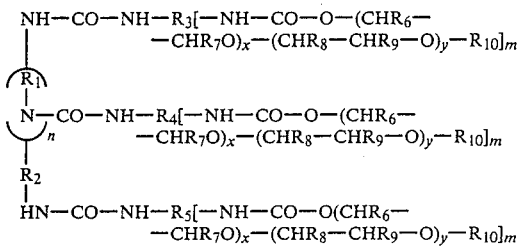

wherein $R_1$ and $R_2$ independently represent $C_2$-$C_4$alkylene or $C_3$-$C_{14}$cycloalkylene, $R_3$, $R_4$ and $R_5$ independently represent optionally substituted alkylene, cycloalkylene or arylene, $R_6$, $R_7$, $R_8$ and $R_9$ independently represent hydrogen or methyl, $R_{10}$ represents $C_1$-$C_{18}$alkyl, $C_6$-$C_{18}$aryl, $C_7$-$C_{18}$aralkyl or $C_2$-$C_{18}$alkenyl, n represents the values 0 to 50, m represents the values 1 to 4 x represents the values 5 to 100, and y represents the values 0 to 100.

2. Heat sensitizing agents corresponding to the general formula II

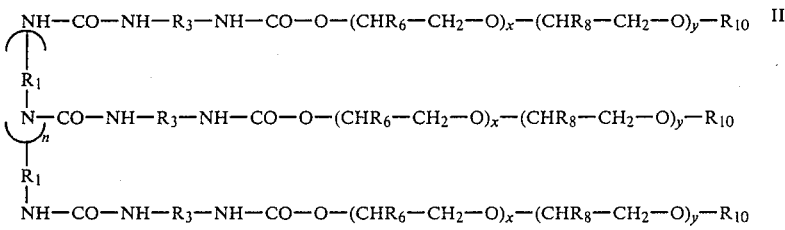

wherein $R_1$ represents $C_2$-$C_7$alkylene or $C_5$-$C_7$cycloalkylene, $R_3$ represents $C_6$-$C_{20}$alkylene or $C_6$-$C_{20}$cycloalkylene or -arylene which may be substituted by $C_1$-$C_4$alkyl or halogen, $R_6$ and $R_8$ represent hydrogen or methyl, $R_{10}$ represents $C_1$-$C_6$alkyl, n represents the values 0 to 5, and x and y represent the values 5 to 100, and the units ($CHR_6$—$CH_2$—O) and ($CHR_8$—$CH_2$—O) are present in blocks, or are statistically distributed or are partially in blocks and partially statistically distributed.

3. Heat sensitizing agents according to claim 2 wherein $R_1$ represents $C_2$-$C_3$alkylene, $R_3$ represents $C_6$-$C_{13}$alkylene, $C_6$-$C_{13}$cycloalkylene or $C_6$-$C_{13}$arylene which may be substituted by methyl, $R_6$ represents hydrogen, $R_8$ represents methyl, n represents the values 1 to 5, x represents the values 5 to 50, and y represents the values 5 to 40, and the units ($CH_2$—$CH_2$—O) and ($CH(CH_3)$—$CH_2$—O) are statistically distributed or are partially in blocks and partially statistically distributed.

4. Process for the preparation of the compounds of claim 1 comprising reacting (m+1) valent polyisocyanates with polyethers corresponding to formula (III)

$$HO-(CHR_6-CHR_7-O)_x-(CHR_8-CHR_9-O)_y-R_{10} \quad \text{III}$$

and with polyamines corresponding to formula IV $$NH_2-(R_1-NH)_n-R_2-NH_2, \quad \text{IV}$$

wherein the radicals $R_1$, $R_2$, $R_6$, $R_7$, $R_8$, $R_9$, and $R_{10}$ and the values m, n, x and y are as defined in claim 1.

5. Process for the production heat-sensitizable latices comprising adding compounds according to claim 1 to the latices.

6. Process according to claim 5 comprising adding 1 to 20 percent, by weight, based on polymer, of the compounds according to claim 1 to the latices.

* * * * *